(12) United States Patent
Grubisha

(10) Patent No.: US 9,049,889 B2
(45) Date of Patent: Jun. 9, 2015

(54) PROTECTIVE HALF SOCK FOR USE IN MULTI-STAGE RECOVERY

(76) Inventor: Tammy Grubisha, Salida, CO (US)

( * ) Notice: Subject to any disclaimer, the term of this patent is extended or adjusted under 35 U.S.C. 154(b) by 226 days.

(21) Appl. No.: 13/226,884

(22) Filed: Sep. 7, 2011

(65) Prior Publication Data

US 2012/0054945 A1     Mar. 8, 2012

Related U.S. Application Data

(60) Provisional application No. 61/380,614, filed on Sep. 7, 2010.

(51) Int. Cl.
*A43B 17/00* (2006.01)
*A41B 11/10* (2006.01)
*A61F 13/08* (2006.01)

(52) U.S. Cl.
CPC ................ *A41B 11/10* (2013.01); *A61F 13/08* (2013.01)

(58) Field of Classification Search
CPC .... A41B 11/003; A41B 11/04; A41B 11/121; A41B 11/123; A41B 11/12; A41B 11/00; A51F 13/08
USPC ......... 2/239; 66/194, 172 R, 172 E, 185, 188, 66/197, 200; 602/3
See application file for complete search history.

(56) References Cited

U.S. PATENT DOCUMENTS

| | | | |
|---|---|---|---|
| 246,454 A | | 8/1881 | Bruen |
| 967,585 A | * | 8/1910 | Teufel ............................ 602/60 |
| 1,330,315 A | | 2/1920 | Hagan |
| 1,373,880 A | * | 4/1921 | Garon ............................. 57/225 |
| 1,726,441 A | | 8/1929 | Loven |
| 1,889,716 A | | 11/1932 | Walker |
| 2,061,160 A | | 11/1936 | Kendall |
| 2,099,539 A | * | 11/1937 | Shively .......................... 66/182 |
| 2,237,145 A | * | 4/1941 | Houseman ....................... 66/14 |
| 2,248,303 A | * | 7/1941 | Morgenroth et al. ............. 2/239 |
| 2,252,769 A | * | 8/1941 | Houseman ....................... 66/14 |
| 2,314,359 A | | 3/1943 | Masterson |
| 2,391,064 A | | 12/1945 | McCandless |
| 2,412,087 A | | 12/1946 | Herbert |
| 2,674,740 A | | 4/1954 | Kidd |
| 2,810,214 A | | 10/1957 | Wolfe |
| 3,040,740 A | * | 6/1962 | Parker ............................... 602/8 |
| 3,334,356 A | | 8/1967 | Abel |
| 3,451,232 A | | 6/1969 | Belzidsky |
| 3,487,830 A | | 1/1970 | Pruett |

(Continued)

OTHER PUBLICATIONS

KnitWiki (1×1ribbing) "http://www.knitting-and.com/wiki/1×1_ribbing" Last modified on May 12, 2007.*

(Continued)

*Primary Examiner* — Khoa Huynh
*Assistant Examiner* — Anna Kinsaul
(74) *Attorney, Agent, or Firm* — Lathrop & Gage LLP

(57) ABSTRACT

A protective half sock for use in multi-stage recovery includes a sock body constructed of a rib knit with Terry cushion, and a knitted posterior welt configured with the sock body and defining a rear opening for insertion of a limb. The sock body may be constructed of a 3×1 rib knit with Terry cushion. The knitted posterior welt may be formed by a 1×1 rib knit. The half-sock includes wool fibers, polyester-coated elastomeric fibers, polyester fibers, and nylon fibers. The cross stretch of the welt is less than the cross stretch of the body.

14 Claims, 3 Drawing Sheets

100

(56) References Cited

U.S. PATENT DOCUMENTS

| | | | |
|---|---|---|---|
| D219,136 S | 11/1970 | Mace | |
| 3,773,041 A | 11/1973 | Bogar, Jr. et al. | |
| 3,820,254 A | 6/1974 | Kopacsi | |
| 3,887,946 A | 6/1975 | Laskin et al. | |
| 4,021,860 A * | 5/1977 | Swallow et al. | 2/239 |
| 4,061,138 A | 12/1977 | Bernstein | |
| 4,078,266 A | 3/1978 | Brown | |
| 4,631,755 A * | 12/1986 | Zingg et al. | 2/239 |
| 4,646,727 A | 3/1987 | Chambers | |
| D291,622 S | 9/1987 | Gray | |
| D294,996 S | 4/1988 | Holmes | |
| 5,070,630 A | 12/1991 | Edmundson | |
| 5,083,557 A | 1/1992 | Lennon et al. | |
| D331,830 S | 12/1992 | Unverferth | |
| D339,422 S | 9/1993 | Williams | |
| 5,575,013 A | 11/1996 | Krack | |
| D385,039 S | 10/1997 | Kesling et al. | |
| D412,781 S | 8/1999 | Richardson | |
| 6,044,497 A | 4/2000 | Richardson | |
| 6,047,403 A | 4/2000 | Juozaitis | |
| D425,289 S | 5/2000 | Sheppard, Jr. | |
| 6,298,496 B1 | 10/2001 | Evans | |
| D454,395 S | 3/2002 | Stephens | |
| 6,393,620 B2 | 5/2002 | Hatch et al. | |
| D488,918 S | 4/2004 | Mays et al. | |
| D493,030 S | 7/2004 | Bartee | |
| 6,931,767 B2 | 8/2005 | Royle | |
| 6,932,784 B1 | 8/2005 | Reading | |
| 7,028,509 B2 * | 4/2006 | Mitchell et al. | 66/176 |
| 7,775,069 B1 * | 8/2010 | Hermanson et al. | 66/186 |
| 8,490,218 B1 * | 7/2013 | Thompson | 2/239 |
| 2005/0144703 A1 * | 7/2005 | Hilbert | 2/239 |
| 2007/0113593 A1 * | 5/2007 | Jeong | 66/180 |
| 2008/0132822 A1 * | 6/2008 | Hermanson et al. | 602/63 |
| 2008/0295230 A1 * | 12/2008 | Wright et al. | 2/455 |
| 2009/0211585 A1 * | 8/2009 | Cumbie et al. | 128/849 |
| 2010/0050321 A1 * | 3/2010 | Martini | 2/239 |

OTHER PUBLICATIONS

ColonialMedical.com—Cast Sock, http://www.colonialmedical.com/product.php?printable=Y&productid=16463 Accessed on the Internet May 7, 2012, 2 pages.

Royal Knit Orthotic Brace/Cast Sock, http://www.royalknit.com/products/brace-cast-socks/ Accessed on the Internet May 7, 2012, 2 pages.

Piggy Warmer Cast Sock toe cover, http://www.piggywarmer.com/castsocks.html, Accessed on the Internet May 7, 2012, 2 pages.

\* cited by examiner

PROTECTIVE HALF SOCK FOR USE IN MULTI-STAGE RECOVERY

RELATED APPLICATIONS

This application claims priority to U.S. patent application Ser. No. 61/380,614, filed Sep. 7, 2010, and incorporated herein by reference.

BACKGROUND

When casting a leg injury, the cast often terminates proximate the toes, leaving the toes free. While such a cast beneficially allows for assessment and monitoring of "the five P's" (pulse, pallor, paresis, paresthesia, and pain), the uncovered toes are left vulnerable to injury, environmental contaminants, and cold.

Following casting or dressing after surgery or injury, patients face the challenge of keeping their toes and/or feet warm and protected. When the patient is mobile, blankets and other loose insulating layers become problematic and potentially dangerous. If a patient tries to use conventional socks as coverings, the patient is faced with the awkwardness and discomfort of pulling an entire sock over an injured or sensitive area, as well as the reality that conventional socks do not allow for the added girth of casts, splints, and surgical dressings. Another challenge arises when the patient tries to sleep, as the weight of blankets and bedding can result in mild discomfort-to-severe pain to the injured areas. In addition, a patient will also undergo several stages of recovery, and the challenge of protecting and warming the toes requires multiple solutions as the recovery situation changes (e.g., as a full cast is replaced by a walking cast, splint, and/or less rigid support such as elastic wrappings).

Various attempts have been made to address the problem of vulnerable toes, however, these attempts have not yielded an optimal solution. For example, U.S. Pat. No. 4,078,266 to Brown discloses a cast sock, however, it relies upon internal gripping features for detachably securing to gripping features of an adhesive strip that is applied directly to the perimeter of the cast. U.S. Pat. No. 2,412,087 discloses a toe protector, however, it is meant to provide a snug fit only inside a sock or stocking, and not over a cast. U.S. Pat. No. 6,044,497 to Richardson discloses a sewn half sock for covering the anterior portion of the foot. The sock includes side seams— potential irritants to bare skin—and consists primarily of a neoprene material, which is limited in its ability to stretch over a cast opening. U.S. Pat. No. D454,395 to Stephens depicts a sewn cast sock that requires a heel strap to stay in place over the toes. Likewise, U.S. Pat. No. 6,932,784 discloses a sewn protective cover for an injured limb, requiring a strap and hook and loop fastener as commonly sold under the trademark Velcro® to stay in place. U.S. Pat. Nos. Des. 339,442 and Des. 219,136 also disclose toe/cast covers relying upon heel straps to maintain their position on the foot. U.S. Pat. No. Des. 385,039 requires not only a heel strap but also a toggle and cord running across the front of the toes for adjusting fit of the disclosed toe cover. Colonial Medical Assisted Devices' cast sock is a full sock design, which is more difficult to apply than a half sock as it must be dragged over the toes and foot that may be painful or sensitive. Xero Sox® provides an oversized rubber, waterproof bag for wearing over casts and dressings, however, it is not meant for daily wear or warmth.

Half socks are also manufactured specifically for dance, yoga, and fashion. However, these socks must be thin to allow the toes to feel and grip the floor through the sock or fit inside close fitting dress shoes, and therefore provide only limited warmth. Further, dance or yoga or fashion half socks may have insufficient cross stretch to fit over a cast, as they are meant to snugly fit a wearer's toes.

SUMMARY

The invention disclosed herein addresses and remedies the above-noted problems of conventional half socks by providing a half sock with enhanced cross stretch, compression, cushioning, and warmth, to see a patient through all stages of recovery. The half sock disclosed herein requires no straps, hook and loop fastener, such as that commonly sold under the trademark Velcro®, cords, or other fasteners to stay in place, and fits comfortably over dressings, casts, and splints and comfortably inside bunion shoes, walking cast boots, and splints. Enhanced cross stretch and compression allow for touch-free, minimal-effort application over sensitive toes and feet, as opposed to standard full socks that are dragged over these areas when applied.

In one embodiment, a protective half sock for use in multi-stage recovery includes a sock body constructed of a rib knit with Terry cushion, and a knitted posterior welt configured with the sock body and defining a rear opening for insertion of a limb.

In another embodiment, a protective half sock for use in multi-stage recovery includes a sock body constructed of a 3×1 rib knit with Terry cushion, and a 1×1 rib knit posterior welt configured with the sock body and defining a rear opening for insertion of a limb. The half-sock includes wool fibers, polyester-coated elastomeric fibers, polyester fibers, and nylon fibers.

DETAILED DESCRIPTION

Figure 1:
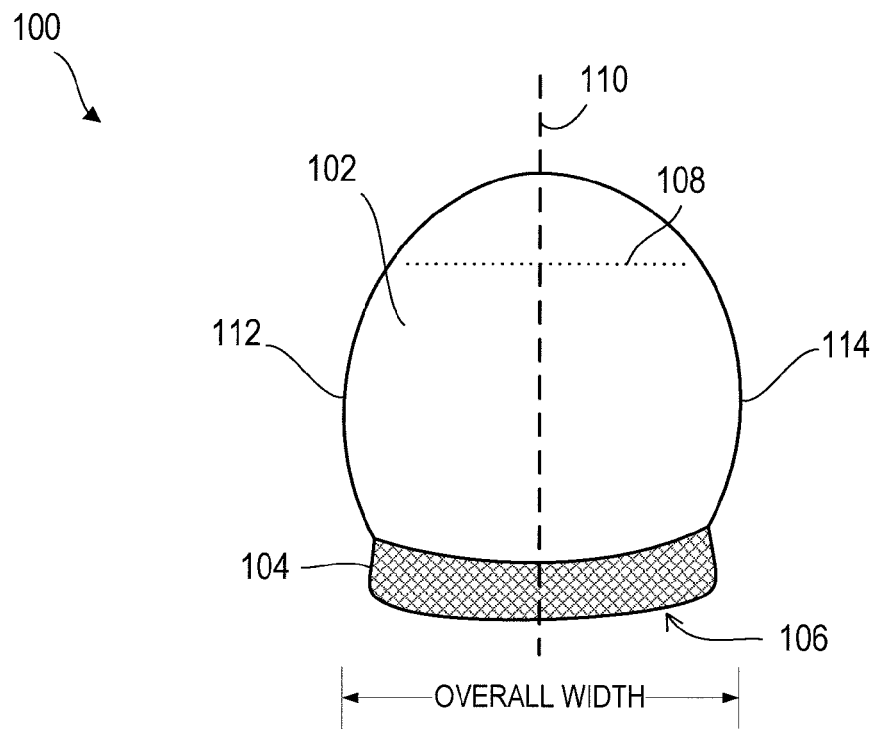
FIG. 1 is a simplified top view of a protective half sock for use in multi-stage recovery, according to an embodiment.

FIG. 1 shows a half sock 100 for use in multi-stage recovery, including a rib knit foot portion, or "sock body" 102 terminating in a posterior welt 104 that defines a rear opening 106 for insertion of a foot or other limb. A flat toe seam 108 closes sock body 102. Yarn forming sock body 102 may be a combination of wool, nylon, polyester coated elastomeric fibers, polyester fibers, merino wool, or other yarn suitable for forming a warm sock body having the stretch of body 102. Half sock 100 is sized to cover the anterior limb of the foot, for example, reaching the upper arch of a bare foot just below the ankle joint and extending beneath the foot to just in front of the heel. As half sock 100 terminates below the ankle, compression of vessels about the ankle area and subsequent impedance of blood flow (and further chill) to the toes is advantageously avoided. Half sock 100 has a lower profile (i.e., is smaller and less bulky) than conventional options, thus calling less attention to itself and also allowing easy sterilization in an autoclave where used in a hospital or other clinical setting.

Half sock 100 may be coated with a soil-resistant coating, or soil-resistant yarns may be used in its construction. The top portion of the sock surface, or the entire surface of half sock 104, may be a denser knit including a snag-resistant yarn (i.e., nylon or nylon-coated fibers) to guard against snagging on hook and loop fasteners, such as those commonly sold under the trademark Velcro® and other rough closures or edges on casts, walking casts, other supportive wrappings, or user-worn medical devices.

In one embodiment, a mid-sized half sock 100 weighs about one ounce (30 grams), has an overall length of between 5 and 6 inches, an overall width of approximately 4.25 inches, and a welt length of about 1.25 inches, when relaxed. The size of welt 104 enhances compression along opening 106 to aid in keeping half sock 100 in place over a cast, splint, or other dressing. Cross stretch is typically measured using a force of ten pounds to stretch the sock in a cross direction. Table 1 shows exemplary cross stretch, measured at ten pounds of force, for each of a plurality of prototype half sock sizes according to the present Application.

TABLE 1

Cross Stretch at 10 Pounds

| Size | Relaxed Length | Relaxed Width | Welt Cross Stretch | Body Cross Stretch |
| --- | --- | --- | --- | --- |
| X-Small | 4.5" | 3.25" | 8.25" | 8.5" |
| Small | 5" | 3.625" | 8.75" | 9.25" |
| Medium | 6" | 4.25" | 9.25" | 10.5" |
| Large | 6.75" | 4.5" | 10" | 11.5" |
| X-Large | 7.875" | 4.75" | 10.5" | 11.75" |

As shown in Table 1, welt cross stretch is less than the body cross stretch for each size of the respective half sock represented in the Table. For conventional socks, the cross stretch of the welt is larger than the cross stretch of the body. According to the present Application though, a lesser cross stretch of welt 104, as compared with sock body 102, further aids in keeping half sock 102 in place, and may be achieved, for example, by using a lesser amount of elastomeric material than is used in forming sock body 102, and/or a different knit. As shown in Table 1, half sock 100 may be provided in larger or smaller sizes, and weight and dimensions may vary accordingly without departing from the scope hereof.

Half sock 100 has, for a ten pound force, a top-to-toe seam cross stretch of between 9 and 10 inches, a welt 104 cross stretch of between 8 and 9.5 inches and a foot cross stretch of between 9.5 and 10.5 inches. Sock body 102 is, for example, knitted with a 3×1 rib with an internal Terry cushion, using thick yarn and relatively long Terry loops (for example, having no less than a 0.25" loop height). Such a knit is not conventionally used in the "foot" section of socks. In one embodiment, half sock 100 is knitted from wool, a double covered polyester-coated spandex blend fiber, polyester fiber, and nylon fiber. The spandex may be air-coated or otherwise treated with polyester.

In the mid-sized half-sock example (having the dimensions and weight listed above), half sock 100 is between about 80-90% wool, between 1-10% nylon, between 1-10% polyester and between 1-2% spandex. Nylon is for example used along the outer surface of welt 104, to prevent snagging on a cast or other supporting device, and optionally, along part or all of the outer surface of sock body 102. Welt 104 may be knitted such that it is coated with nylon, whereas nylon can be used along a portion of outer sock body 102 (i.e., proximate welt 104). Welt 104 may be constructed of a 1×1 rib knit.

In the mid-sized half-sock example, the wool may have a worsted yarn count of between 1/7.5 and 1/10.7. Wool having a worsted yarn count of approximately 4.97/1 and 7.14/1 may be used in addition to, or as an alternative to, the 1/7.5-1/10.7 wool. The nylon used in half sock 100, for example, has a yarn count of between 2/242 and 46/72. In another example, half sock 100 is fabricated using a super-washed Merino wool with a worsted yarn count of 1/16, a 20 denier Lycra air tacked with a polyester with a yarn count of 1/150, a Nylon with a yarn count of 1/70, and a polyester with a yarn count of 3/70. These thread and yarn counts are exemplary and other thread and yarn counts may be used without departing from the scope hereof.

It will be appreciated by those of ordinary skill in the art, after reading and comprehending the present Application, that other rib configurations (for body 102), non-rib constructions (for welt 104), fibers that provide warmth (for example wool, wool blend or synthetic fibers), and fibers that provide the cross stretch features above (for example, another elastomeric material in place of the spandex) may be used without departing from the scope hereof. Yarn counts and percent composition of half sock 100 may vary likewise vary without departing from the scope hereof. In one example, a half sock includes 60-95% wool, 1-40% nylon, 1-15% polyester and 1-10% spandex. However, percent composition may also vary according to intended season (e.g., warm season or cool season) and desired features (e.g., more or less snag resistance) of half-sock 100. Half sock 100 may be produced on a dial and cylinder circular knitting machine, and yarns may be used in various concentrations or in different stitches or loops at different stages of the knitting process. For example, nylon yarn may be raised to the surface of sock body 102 and/or welt 104 to reduce snagging, as described above.

It will be appreciated that smaller and larger sized half-socks may have differing yarn counts, loop length, and percent composition from those listed above in the mid-sized half sock example.

Figure 2:
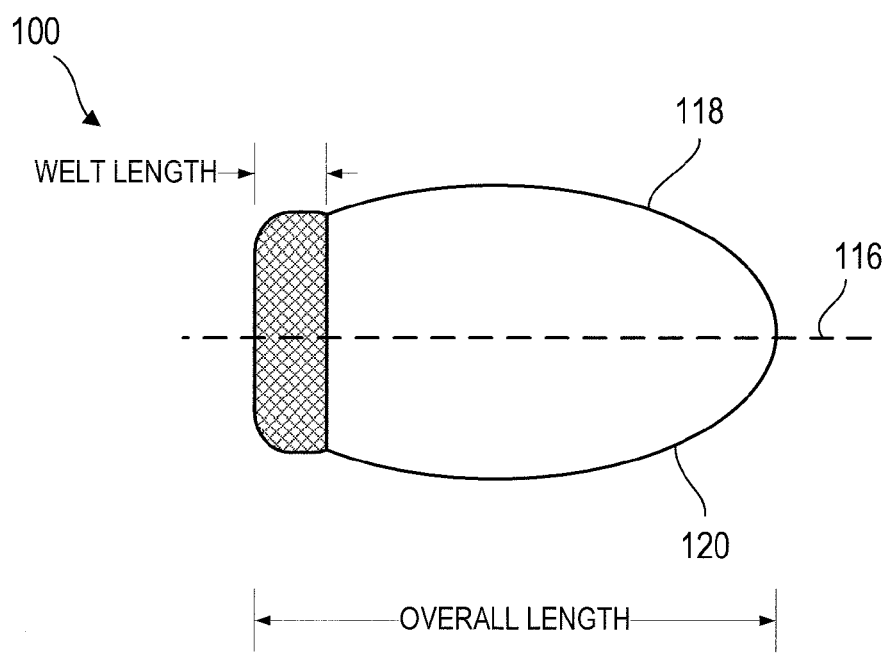
FIG. 2 is a simplified side view of the half sock of FIG. 1.
Figure 3A:
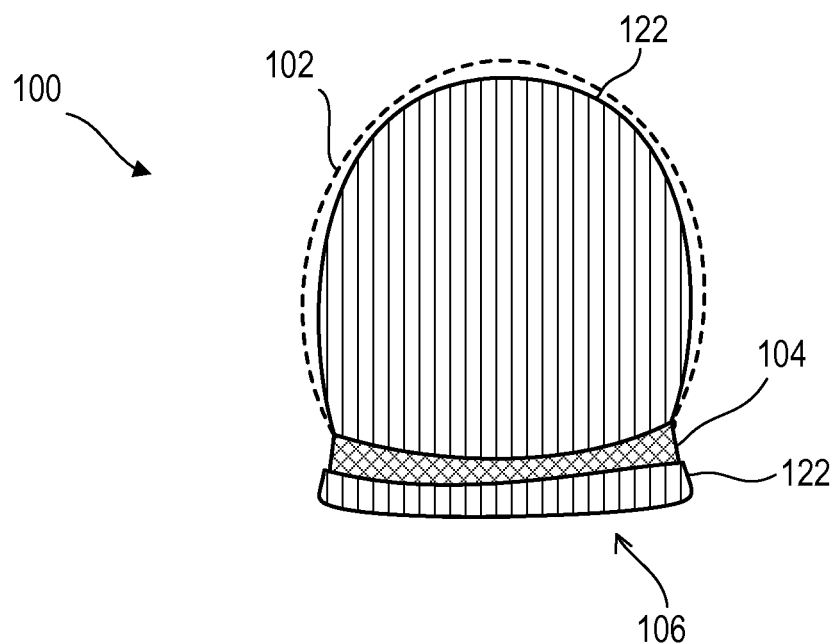
FIG. 3A is a top view of the half sock of FIGS. 1 and 2 showing an internal liner, according to an embodiment.
Figure 3B:
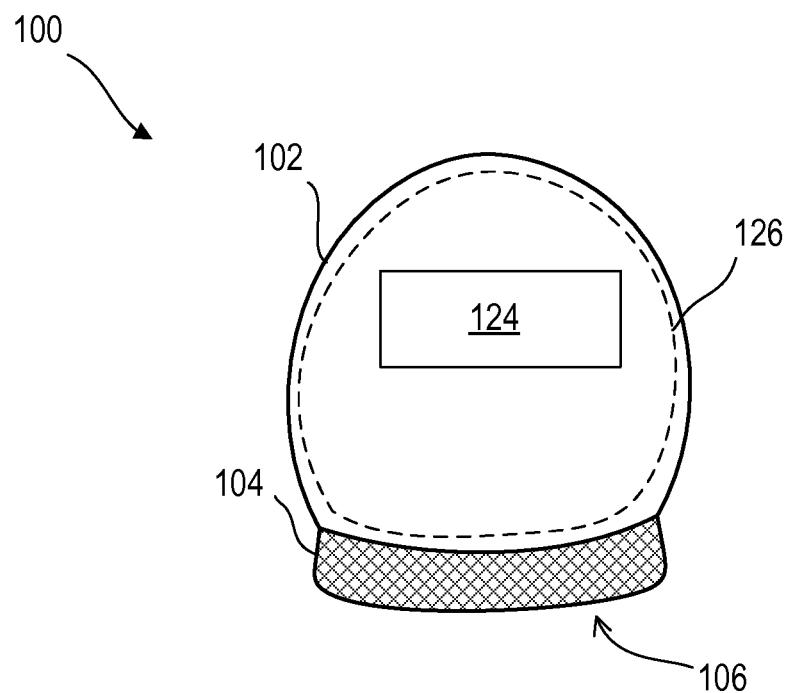
FIG. 3B is a bottom view of the half sock of FIGS. 1 and 2, showing an anti-skid pad or treatment, according to an embodiment.

Half sock 100 has left/right and top/bottom symmetry, allowing half sock 100 to be worn on either a left or right foot. For example, when longitudinally divided along the top (see dashed line 110), left side 112 and right side 114 of half sock 100 are substantially symmetrical. As shown in FIG. 2, when longitudinally divided along a side (see dashed line 116), top half 118 and bottom half 120 are substantially symmetrical.

Where half sock 100 is knitted of wool, a cotton or synthetic liner 122 (shown in FIG. 3A) may be sewn or otherwise secured within half sock 100, to prevent direct contact between wool and the skin of patients who react or are allergic to wool. Liner 122 may be any hypoallergenic or low-sensitivity fabric so long as it has sufficient cross stretch not to impede cross stretch of half sock 100. Liner 122 is, for example, sized to extend beyond welt 104 such that it may be rolled over and secured to welt 104 outside of half sock 100, to prevent liner 122 from creeping into sock body 102 and to further prevent contact between skin and wool or other allergenic yarn of half sock 100. As illustrated in FIG. 3B, a non-skid pad or treatment generally represented by box 124 may be applied to the underside or bottom surface of half sock 100, generally bounded by dashed line 126.

Figure 4A:
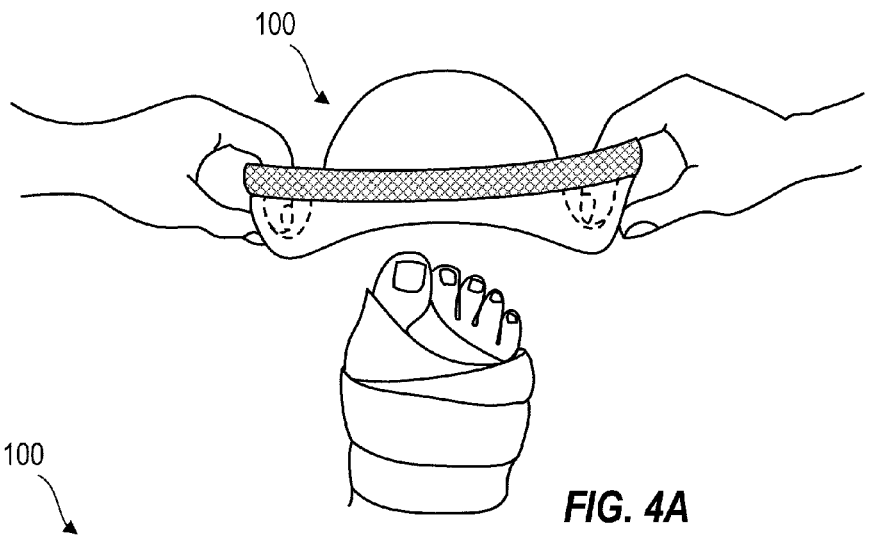
FIGS. 4A-4C illustrate touch-free application of the half sock of FIGS. 1-3, according to an embodiment.
Figure 4B:
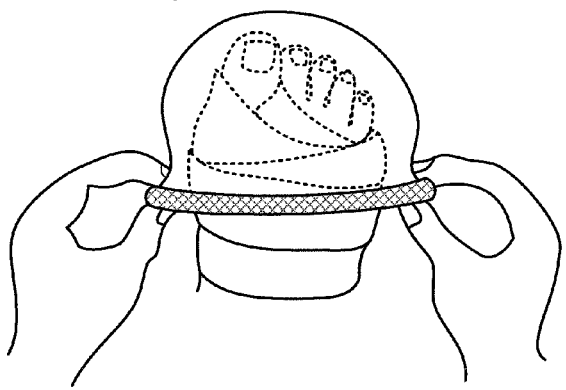
Figure 4C:
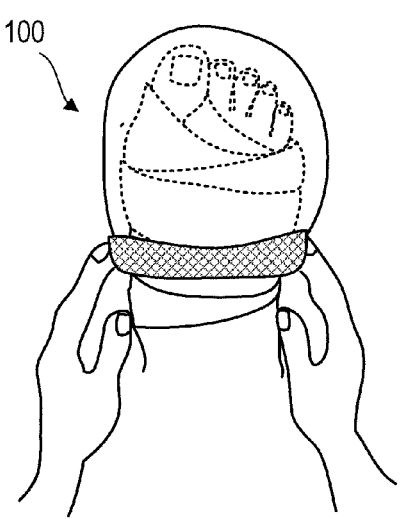

FIGS. 4A-4C illustrate touch-free application of half sock 100. In one example of practice, a user places his or her fingers within welt 104 or sock body 12 and turns a portion of half sock 100 inside-out, as best seen in FIG. 4A. As shown in FIG. 4B, after placing half sock 100 over the limb in question (i.e., the foot, as shown), the user unrolls half sock 100 to further cover the limb and secure half sock 100 in place (FIG. 4C). Half sock 100 may likewise be removed with minimal contact.

Enhanced cross stretch provided by the 3×1 rib knit with Terry cushion of sock body 102 allows the user to stretch, place, and release half sock 100 over the limb without dragging a tight covering over sensitive skin outside of a cast or other protective covering. In addition to the wool content, density of the knit enhances warmth of half sock 100, allowing a patient to sleep or rest comfortably with the limb protruding from bedding. For example, the patient's feet remain warm and protected without suffering the uncomfortable or even painful pressure exerted by blankets or other bedding. The compression, cross stretch, thickness, cushioning, sizing and knit of half sock 100 yield a medical recovery sock that is adaptable to and useful in all phases of a patient's recovery. For example, half sock 100 stretches to allow touch-free application and/or to cover the terminal part of a cast or other protective wrappings. Compression provided by the fiber combination in half sock 100 (for example, by the spandex) keeps the sock in place without any extra straps, hook and loop fasteners, such as those commonly sold under the trademark Velcro®, cords, adhesive or other fasteners. Moreover, half sock 100 fits comfortably inside bunion shoes, walking cast boots, and splints. Compression features of half sock 100 also allow the sock to return to its normal, relaxed dimensions after being stretched, such that a same half sock 100 may first be worn over the terminal part of a cast, then over lighter wrappings (and/or inside a walking cast), and then on the patient's bare foot.

Though not shown in the drawings, sock body 102 may include a hill-and-valley construction along the anterior edge to conform more closely to a particular wearer's toes. Materials of half sock 100 may also be chosen according to climate—for example, lighter-weight yarn may be used in a summer/warm-temperature sock, whereas heavier, denser yarns may be selected for a winter/cold-temperature sock. It will be appreciated that half sock 100 is not limited to medical uses, but may be worn as easy-on slippers or as an extra layer for cold weather camping, winter sports, or in other environments where extra warmth or foot protection is desired.

While the present invention has been described above, it should be clear to one of ordinary skill in the art that changes and modifications may be made to the process and product described herein without departing from the spirit and scope of the invention. For example, alternate rib with Terry cushion knits may be used in sock body 102, such as a 2×1, 4×1, and/or 5×1 rib knit. Likewise, an alternate knit may be used in place of the 1×1 knit of welt 104. Measurements provided are exemplary and measurements may vary due to inconsistencies with natural fibers and with other variations in production.

What is claimed is:

1. A protective half sock for use in multi-stage recovery, comprising: a sock body constructed of a rib knit with terry cushion, the rib knit having a first cross-stretch, the sock body being sized for covering the distal portion of a foot; and a knitted posterior welt adjoining the sock body, defining a rear opening for insertion of a limb, and comprising a second knit having a second cross-stretch, the welt being sized for positioning over a region of a cast, bandage or dressing located between a toe and a heel of the foot; wherein: the first cross-stretch exceeds the second cross-stretch such that a stretched width of the sock body exceeds a stretched width of the welt when both the sock body and welt are stretched by a constant force, the posterior welt is less elastic than the sock body, the sock body and the welt are formed from the same percent composition of material, and wherein the percent composition of material comprises at least between 1 and 40% nylon, between 1 and 15% polyester, and between 1 and 10% spandex.

2. The half sock of claim 1, the sock body constructed of a 3×1 rib with Terry cushion and having a cross stretch of between 9.5 and 10.5 inches for a relaxed width of 4.25 inches.

3. The half sock of claim 1, the welt constructed of a 1×1 rib knit and having a cross stretch of between 8 and 9.5 inches for a relaxed width of 4.25 inches.

4. The half sock of claim 1, the sock body comprising wool, polyester-coated elastomeric fibers, polyester fibers, and nylon fibers.

5. The half sock of claim 4, the elastomeric fibers comprising spandex.

6. The half sock of claim 4, the wool comprising worsted wool, raw merino wool, or pre-shrunk super-washed merino wool.

7. The half sock of claim 4, the wool having a worsted yarn count of between 1/7.5 and 1/10.7, and the nylon having a yarn count of between 2/242 and 46/72.

8. The half sock of claim 1, the welt comprising wool, polyester-coated elastomeric fibers, polyester fibers, and nylon fibers.

9. The half sock of claim 1, the half sock having, when relaxed, an overall length of between 5-6 inches, an overall width of about 4.25 inches and a welt length of about 1.25 inches.

10. The half sock of claim 1, the percent composition of material further comprising:
between 60 and 95% wool.

11. A protective half sock for use in multi-stage recovery, comprising:
a sock body constructed of a 3×1 rib knit with terry cushion, the rib knit having a first cross-stretch, the sock body being sized for covering the distal portion of a foot; and
a 1×1 rib knit posterior welt adjoining the sock body, defining a rear opening for insertion of a limb, and comprising a second knit having a second cross-stretch, the welt being sized for positioning over a region of a cast, bandage or dressing located between a toe and a heel of the foot; wherein:
the first cross-stretch exceeds the second cross-stretch such that a stretched width of the sock body exceeds a stretched width of the welt when both the sock body and welt are stretched by a constant force,
the posterior welt is less elastic than the sock body,
the half-sock includes wool fibers, polyester-coated elastomeric fibers, polyester fibers, and nylon fibers, and
the sock body and the welt are formed from the same percent composition of material.

12. The half sock of claim 11, the elastomeric fibers comprising spandex.

13. The half sock of claim 11, further comprising a hypoallergenic internal liner.

14. The half sock of claim 11, the limb comprising a foot, and further comprising an anti-skid treatment or pad on a bottom surface of the sock body.

* * * * *